(12) United States Patent
Grundei

(10) Patent No.: US 6,425,925 B1
(45) Date of Patent: Jul. 30, 2002

(54) LEG EXOPROSTHESIS FOR ADAPTATION TO A THIGH STUMP

(75) Inventor: Hans Grundei, Lübeck (DE)

(73) Assignee: Schütt & Grundei Orthopädietechnik GmbH, Lübeck (DE)

( * ) Notice: Subject to any disclaimer, the term of this patent is extended or adjusted under 35 U.S.C. 154(b) by 0 days.

(21) Appl. No.: 09/411,181

(22) Filed: Oct. 1, 1999

(30) Foreign Application Priority Data

Oct. 1, 1998 (DE) .......................... 198 45 191

(51) Int. Cl.⁷ .............................. A61F 2/60; A61F 2/74; A61F 2/78
(52) U.S. Cl. ........................................ 623/32; 623/27
(58) Field of Search ............................ 623/33, 39, 43, 623/46, 27, 28, 30, 31, 60, 58, 32

(56) References Cited

U.S. PATENT DOCUMENTS

| | | | |
|---|---|---|---|
| 2,568,051 A | | 9/1951 | Catranis |
| 2,588,013 A | * | 3/1952 | Kleinekathofer ............. 623/39 |
| 3,947,897 A | | 4/1976 | Owens |
| 4,143,426 A | | 3/1979 | Hall et al. |
| 4,158,895 A | * | 6/1979 | Reswick et al. ............... 623/57 |
| 4,776,852 A | | 10/1988 | Rubic |
| 5,041,137 A | * | 8/1991 | Nemoshkalov ............. 623/16 |
| 5,139,526 A | * | 8/1992 | Skardoutos et al. .......... 623/59 |
| 5,800,572 A | * | 9/1998 | Loveall ....................... 623/63 |
| 5,888,215 A | * | 3/1999 | Roos et al. ................... 623/33 |

FOREIGN PATENT DOCUMENTS

| | | |
|---|---|---|
| DE | 346255 | 12/1921 |
| DE | 808974 | 7/1951 |
| DE | 42 08 247 C1 | 10/1993 |
| DE | 94 00 720 U | 6/1995 |
| DE | 196 27 994 A1 | 1/1997 |
| DE | 308670 | 11/1997 |
| EP | 0 358 056 B1 | 10/1993 |
| GB | 643734 | 9/1950 |
| GB | 681853 | 10/1952 |
| JP | 01085645 | * 3/1989 .................. 623/16 |

OTHER PUBLICATIONS

"A Future Prostetic Limb Device", Journal of Rehabilitation Research and Development, vol. 22, No. 3, pp. 99–102, Jul. 1985.*

H.H. Wetz, et al, "Amputation und Prothetik", *Orthopäde*, 1998, 27:397–411 (1998).

* cited by examiner

*Primary Examiner*—David H. Willse
*Assistant Examiner*—Alvin Stewart
(74) *Attorney, Agent, or Firm*—Akin, Gump, Strauss, Hauer & Feld, L.L.P.

(57) ABSTRACT

A leg exoprosthesis for adaptation to a thigh stump (1) has an adapter (2) for a knee joint (3), a knee joint (3) mounted thereon, and a lower leg prosthesis (4) coupled to it. On the lower leg prosthesis (4) a force-transmitting element (5) is coupled into which extending forces are introduced.

5 Claims, 3 Drawing Sheets

LEG EXOPROSTHESIS FOR ADAPTATION TO A THIGH STUMP

BACKGROUND OF THE INVENTION

The invention relates to a leg prosthesis which is to be adapted to a thigh stump following amputation.

Basically, there is a distinction between passive and functional or active prostheses. Movements can be executed with the latter which imitate the natural sequence of motion of a healthy leg. The use of myoelectric controls would be theoretically conceivable for this. With these myoelectric controls myosignals are transcutaneously derived from innervated musculature, amplified and used for analog or digital control of electromotors, which can then execute appropriate prosthesis motions. Of course, the energy expenditure with a leg prosthesis is so high that the energy density of known accumulators would not suffice to be able to supply an electric drive motor for the knee joint with electric current for an acceptable period of time.

With so-called internal power prostheses, movements of distant body parts via bandage traction are used to carry out the prosthesis function. Thus, perhaps the forward movement of the shoulder on the non-amputated side can be used for opening the prosthetic hand. Nevertheless, up until now no attempts are known to design a leg prosthetic as an internal power prosthesis.

From U.S. Pat. No. 4,143,426 an implantable adapter is known, which has a porous surface, into which bone material is supposed to grow. This adapter is part of an internal power prosthesis, in which forces are transmitted to a joint via an artificial band. The forces generated originate from the remaining muscles of the carrier of the adapter itself.

From the publication H. H. Wetz et al., "Amputation and Prosthetics," *Orthopedics*, 27:397–411 (1998), myokineplasty according to Sauerbruch is described, which is suitable for this. Shown therein is a connecting element in the form of a stirrup (FIGS. 18, 19 and 20*a, b*), which is supposed to transmit the forces generated by the muscle. However, in the publication this stirrup is tied to the pectoral muscle or the biceps muscle, thus in the shoulder or upper arm area.

SUMMARY OF THE INVENTION

Against this background, an object of the present invention is to develop a proposal for a leg prosthesis in the form of an internal power prosthesis. This object is accomplished in accordance with the invention by a leg exoprosthesis for adaptation to a thigh stump. Advantageous refinements and embodiments are described below and in the dependent claims.

Accordingly, the leg prosthesis comprises an adapter for a knee joint, the knee joint itself, and a lower leg prosthesis coupled to it, wherein the adapter with a proximal stem element, which is at least partially covered with an open-meshed, three-dimensional spatial network structure, is implantable into the tubular bone stump of the thigh stump and is provided on its distal end with a coupling device for the knee joint. A bridle with a connecting element attached on the thigh stump end in the form of a stirrup is coupled to the lower leg prosthesis for tying to the extensor musculature of the thigh, which transmits extensor forces for extending the knee joint.

The extensor forces are generated by the patient himself in the extensor musculature, for example in the quadriceps muscle. The tying of the force-transmitting element to the musculature on the amputation stump takes place according the so-called Sauerbruch myokineplasty.

For this purpose, a muscle channel is formed in the remaining musculature in the amputation stump. By turning a skin flap inwardly, a displaceable muscle channel is successfully laid out such that, for example, an ivory or a glass pin can be guided into it. The patient is in a position, owing to the innervation of the stump musculature, i.e., the quadriceps muscle, to apply appropriate forces and via the muscle canal and a corresponding connecting element to introduce them into the force-transmitting element, and thereby to extend the artificial knee joint appropriately. The connecting element installed on the thigh stump end in the form of a stirrup serves for this purpose.

The bridle mentioned as a force-transmitting element basically replaces the natural patellar ligament and the patellar attachment up to the tibial tuberosity in the healthy leg.

The adapter for the knee joint is installable with a proximal stem element into the tubular bone stump of the thigh stump, wherein the stem element is at least partially covered with an open-meshed, three-dimensional spatial network structure, and is provided on its distal end with a coupling device for the knee joint.

The open-meshed, three-dimensional spatial network structure, which is also characterized as interconnecting, makes it possible for natural bone material to grow into, through, behind and around it during the healing phase, so that the stem element is integrated into the tubular bone after a relatively short time, in any case with respect to the substrate flow, and an extremely stable secondary fixation is guaranteed.

By this construction a sufficiently firm seating of the adapter on or in the thigh stump is guaranteed, which can also withstand the high forces of up to 800 kp introduced into the force-transmitting element.

A previously unknown natural coordinated movement is possible with the leg prosthesis of the invention, owing to the tying of the remaining musculature in the thigh stump directly to the lower leg prosthesis coupled on the knee joint.

However, the knee joint is also constructed in a special way according to a preferred embodiment, and is adapted to the leg prosthesis of the invention. Thus, it is provided that the knee joint has an upper part, which is connectable with the adapter, and has a lower part which is flexibly connected with the upper part. The upper part is supported on the sliding surfaces of the lower part with skids, and the skids are held against the sliding surfaces by the action of a spring. The upper part is swivellable with the skids on the sliding surfaces around a pivot point until reaching an extended position, wherein the vertical main axis of the upper part is shifted forwardly (anteriorly) in relation to the vertical main axis of the lower part. In side view the skids basically have bearing surfaces which, when viewed from front to back (anterior to posterior), assume curvature radii which become ever smaller about the pivot point, and which lie on the sliding surfaces of the lower part, which are substantially flat in construction. The upper part is displaced to the rear (posteriorally) in relation to the lower part with increasing bending of the joint. Further details for this construction can be gathered from European patent EP 0 358 056 B1.

This knee joint is adapted, in an especially suitable manner, for use within the framework of the present invention. Thus, the special construction of the pole curve of the skids of the upper part with the curvature radii which, viewed from front to back, become continuously smaller, makes it possible to imitate the natural force conditions in the knee. Thus, the force transmitted by the force-transmitting element is greatest in the extended position of the knee and smallest in the flexed (bent) position. This corresponds to the natural conditions.

With a pole curve constructed other than as indicated, for example with a circular pole curve, the physiological course of movement of the knee would not be possible at all.

The knee joint known from the cited publication is adapted, in an especially advantageous manner, to use in the framework of the present invention, if the lower part of the knee joint has a frame which supports a carrier for the sliding surfaces, whose upper part is connected by axle journals with braces guided laterally on the frame. The braces are rigidly connected by an axle engaging through oblong holes, and the axle is biased in relation to the frame by a spring and via the braces holds the skids against the sliding surfaces of the lower part. The mentioned force-transmitting element is fastened on the frame of the lower part. The force generated by the quadriceps muscle is thus introduced directly from the thigh stump into the lower part of the knee joint under excess tension of the knee joint itself. This is an exact imitation of the introduction of force through the patellar ligament or patellar attachment in the healthy leg.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

Identical parts are provided with the same reference numerals below.

DETAILED DESCRIPTION OF THE INVENTION

Figure 1:
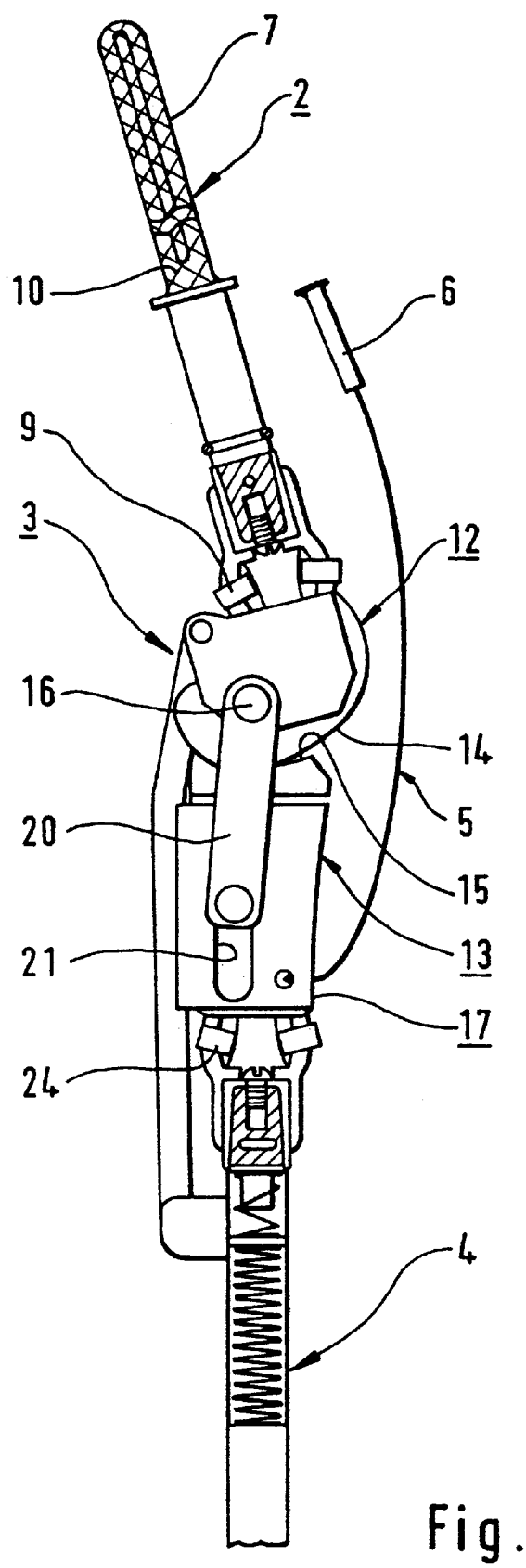
FIG. 1 is a schematic side view of the leg prosthesis according to the invention.
Figure 2:
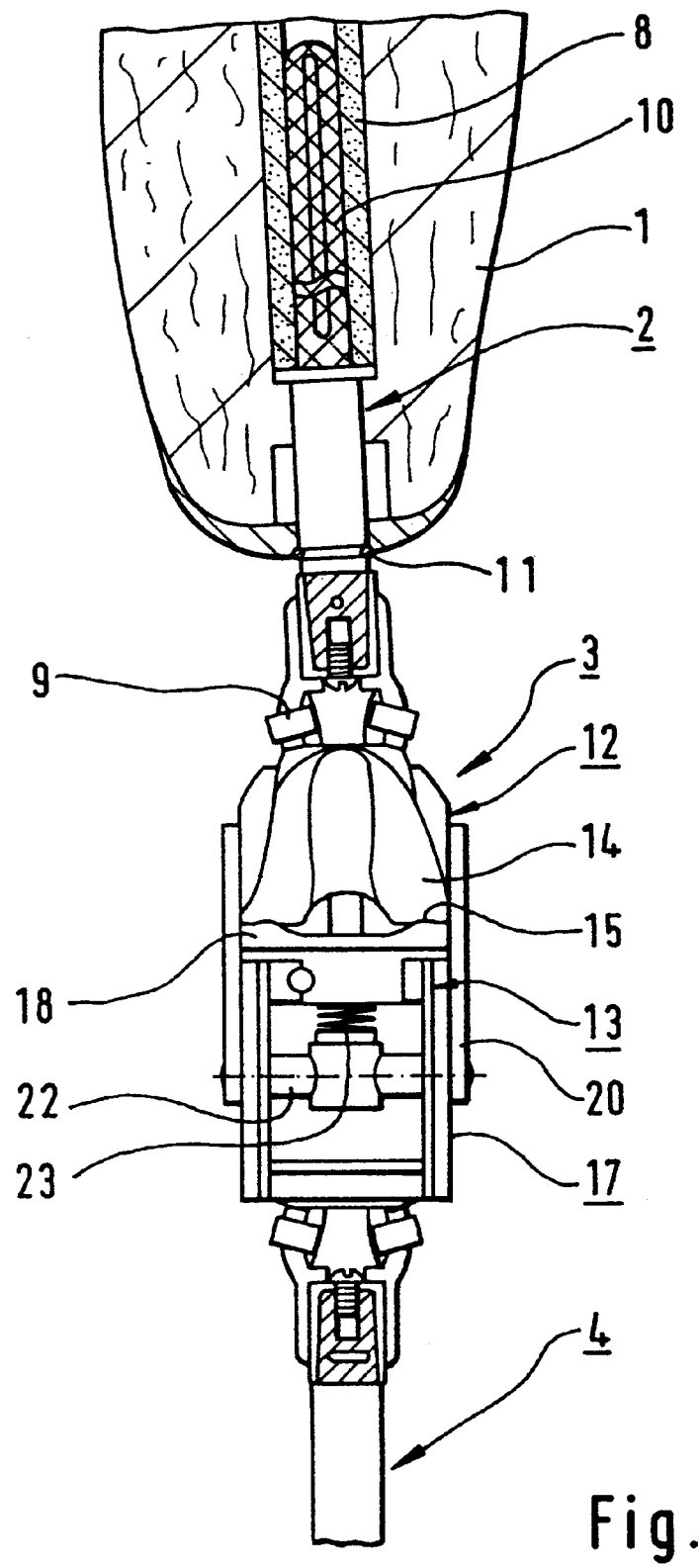
FIG. 2 is a schematic view of the leg prosthesis following operative insertion of the adapter into a thigh stump.

FIG. 1 is a schematic side view of the completely assembled leg prosthesis. This has an adapter 2 which is connected with the thigh stump 1 (FIG. 2). A knee joint 3 is coupled to the adapter 2 by a coupling device 9. The knee joint 3 is connected with a lower leg prosthesis 4 by a further coupling device 24.

The knee joint 3 has an upper part 12 and a lower part 13. The upper part 12 is supported by skids 14 on sliding surfaces 15 of the lower part 13. With movement from the extended state to the flexed state, the upper part 12 swivels about a pivot point 16.

The skids 14 are so constructed and form such a pole curve that they have bearing surfaces in side view which, when viewed from front to back, assume constantly diminishing curvature radii about the pivot point 16. This construction makes possible in the prosthesis the physiological imitation of the force distribution in the natural knee, namely to the extent that the greatest forces must be applied to bring the knee into the extended position, while the smallest forces are necessary for the flexed position.

The lower part 13 has a frame 17 in which oblong holes 21 are present laterally and medially. An axle 22 engages through the oblong holes 21 and rigidly connects braces 20, which are laterally guided on the frame 17, with each other. The axle 22 is herein biased relative to the frame 17 by a spring 23.

The force-transmitting element 5 in this embodiment is attached to the frame 17 of the lower part 13 of the knee joint 3. Its other end is constructed as a stirrup-like connection element 6.

The adapter 2, with its proximal stem element 7 which is covered with an open-meshed, three-dimensional spatial network structure 10, is implanted into the tubular bone stump 8 (see FIG. 2).

A sealing element 11 is seated at the point where the adapter 2 exits form or passes out of the thigh stump 1 and protects the breakthrough point in the extremity of the stump and contributes to the ability to keep the breakthrough point aseptic with ease.

The frame 17 of the lower part 13 of the knee joint 3 further supports a carrier 18 for the sliding surfaces 15.

Figure 3:
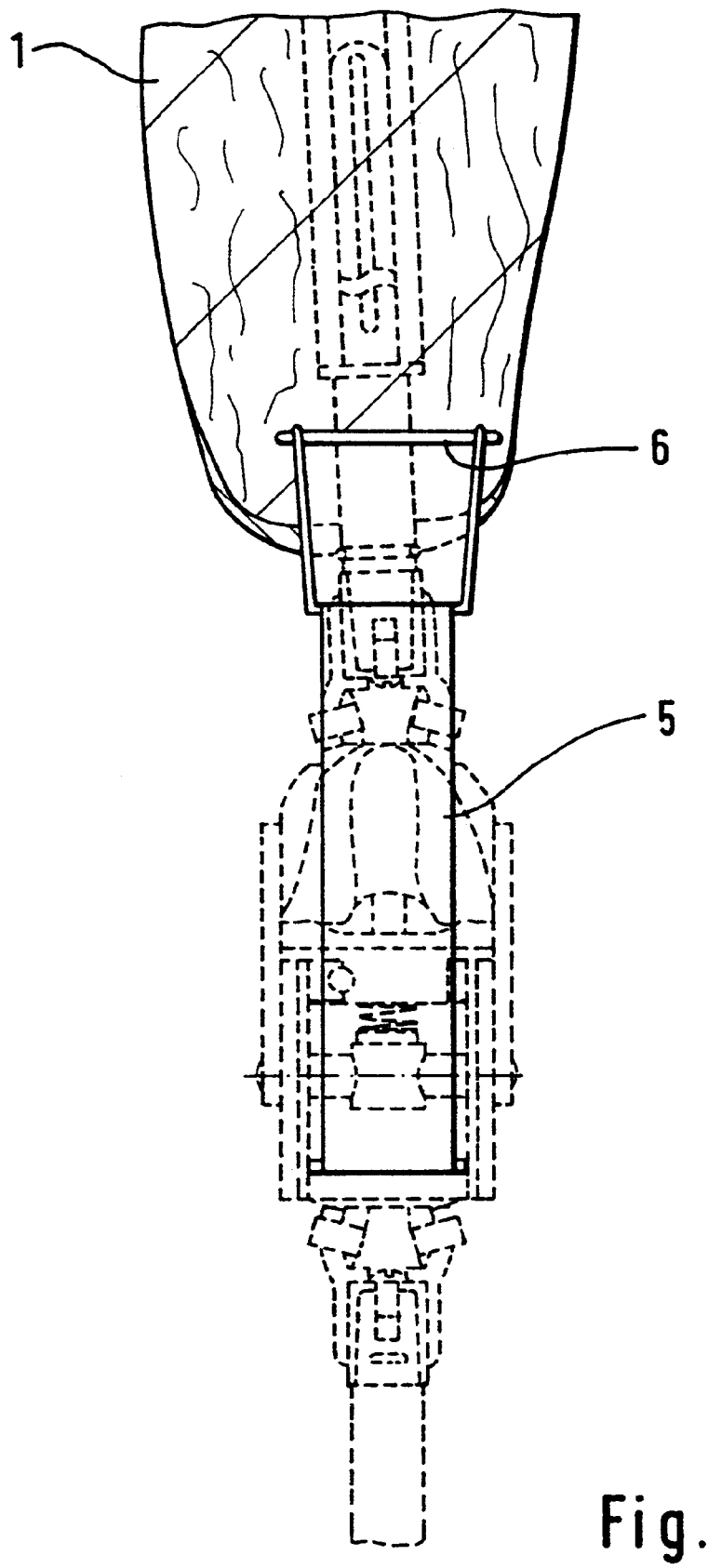
FIG. 3 depicts schematically the position of the force-transmitting element after installation of the prosthesis on a thigh stump.

FIG. 3 is a schematic view from the front, wherein the parts from FIG. 2 are represented in dashed lines for the sake of an overview. This distinctly illustrates that the force-transmitting element 5 is here constructed as a bridle band, wherein the stirrup-like connection element 6 is tied to the extensor musculature, for example the quadriceps muscle, in the aforementioned manner according to the cited Sauerbruch myokineplasty.

The bridle band can be made of a suitable material, such as synthetic fibers, synthetic fiber belt, or even a resistant rubber. The material must in any case be capable of transmitting the relatively high forces arising with each extension movement. These lie in a range up to 800 kp.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. A leg exoprosthesis for adaptation to a thigh stump (1), comprising an adapter (2) for a knee joint (3), a knee joint (3) attached thereto, a lower leg prosthesis (4) coupled on the knee joint (3), the adapter (2) having a proximal intramedullary stem element (7) at least partially covered with an open-meshed, three-dimensional spatial network structure (10) which is implantable into a tubular bone stump (8) of the thigh stump (1), the adapter (2) having a distal end provided with a coupling device (9) for connection to the knee joint, and a force-transmitting element (5) coupled to the lower leg prosthesis (4) for transmitting extensor forces to extend the knee joint (3), the force-transmitting element (5) having on its end applied to the thigh stump a connection element (6) in a form of a stirrup configured to be tied to extensor musculature of the thigh.

2. The leg exoprosthesis according to claim 1, wherein the force-transmitting element (5) comprises a bridle band.

3. The leg exoprosthesis according to claim 1, wherein a sealing element (11) is seated at a point where the adapter (2) exits from the thigh stump (1).

4. The leg exoprosthesis according to claim 1, wherein the knee joint (3) comprises an upper part (12) connectable with the adapter (2) and a lower part (13) flexibly connected with the upper part (12) and connectable with the lower leg prosthesis (4), the upper part (12) being supported with skids (14) on sliding surfaces (15) of the lower part (13), the skids (14) being held against the sliding surfaces (15) by spring action, the upper part (12) being swivellable with the skids on the sliding surfaces (15) about a pivot point (16) until reaching an extended position, wherein a vertical main axis of the upper part (12) is shifted anteriorly in relation to a vertical main axis of the lower part (13), the skids (14) in side view having bearing surfaces which, when viewed anterior to posterior, assume constantly diminishing curvature radii about the pivot point and lie on the sliding surfaces (15) which are substantially flat in construction, and wherein the upper part (12) is displaced posteriorally in relation to the lower part (13) with increasing flexion of the joint.

5. The leg exoprosthesis according to claim 4, wherein the lower part (13) of the knee joint (3) has a frame (17) which supports a carrier (18) for the sliding surfaces (15), the upper part (12) is connected by axle journals with braces (20) laterally guided on the frame (17), the braces (20) being rigidly connected by an axle (22) engaging through at least one oblong hole (21) in the frame (17), wherein the axle (22) is biased by a spring (23) relative to the frame (17) and via the braces (20) holds the skids (14) against the sliding surfaces (15) of the lower part (13), and wherein the force-transmitting element (5) is attached to the frame (17) of the lower part (13).

* * * * *